United States Patent [19]

Jordan

[11] 4,204,423

[45] May 27, 1980

[54] CHROMATOGRAPH

[75] Inventor: John H. Jordan, Beaumont, Tex.

[73] Assignee: Mobil Oil Corporation, New York, N.Y.

[21] Appl. No.: 946,882

[22] Filed: Sep. 28, 1978

[51] Int. Cl.² .......................................... G01N 31/08
[52] U.S. Cl. ................................ 73/23.1; 73/61.1 C; 55/197; 219/10.55 R
[58] Field of Search .......................... 73/23.1, 61.1 C; 219/10.55 R, 10.55 A; 55/67, 197, 386; 422/89; 23/232 C

[56] References Cited

U.S. PATENT DOCUMENTS

| 2,494,716 | 1/1950 | McMahon et al. | 219/10.55 R |
| 3,169,389 | 2/1965 | Green et al. | 73/23.1 |
| 3,232,093 | 2/1966 | Burow et al. | 73/23.1 |
| 3,527,567 | 9/1970 | Philyaw et al. | 73/23.1 |
| 3,778,578 | 12/1973 | Long et al. | 219/10.55 R |

Primary Examiner—Stephen A. Kreitman
Attorney, Agent, or Firm—Charles A. Huggett; Raymond W. Barclay; Richard S. Barth

[57] ABSTRACT

An apparatus for gas and liquid chromatograph in which the chromatographic columns are heated by microwaves is provided.

6 Claims, 1 Drawing Figure

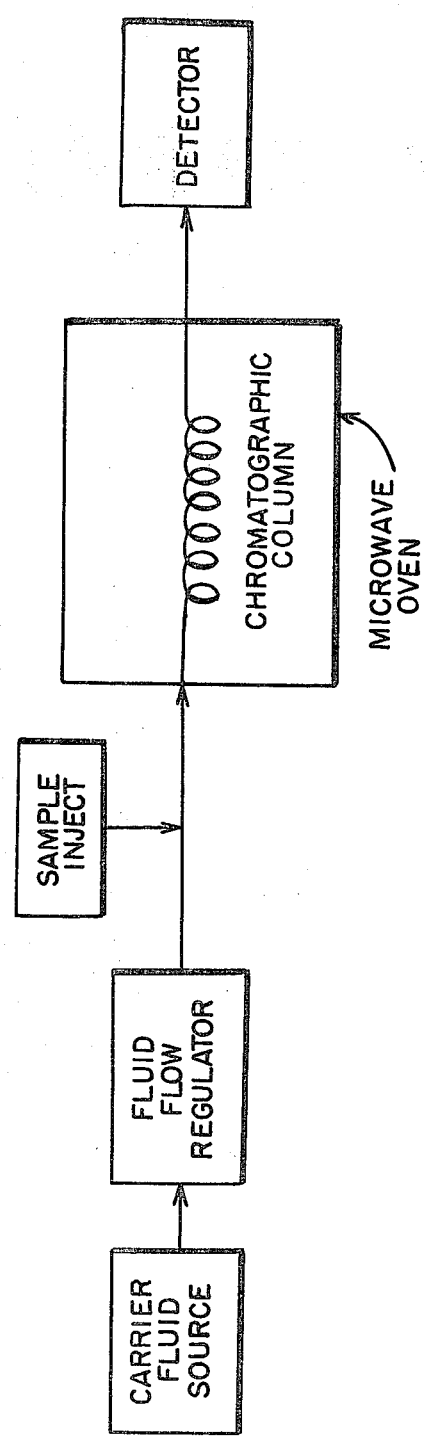

CHROMATOGRAPH

BACKGROUND OF THE INVENTION

1. Field of the Invention

The invention relates to apparatus for gas and liquid chromatography. More particularly, the invention relates to apparatus in which the chromatographic columns are heated by microwave.

2. Description of the Prior Art

Gas and liquid chromatography are physical methods for the separation and identification of chemical compounds. Briefly, gas chromatography is a method in which the components of a mixture are separated from one another by introducing a sample of the mixture into a carrier gas stream which percolates through or along a stationary bed of large surface area. The stationary bed is normally contained within a chromatographic column. The different components of the sample move through the column at different rates and emerge one after the other at the outlet of the column where they are detected and measured. A typical gas chromatograph apparatus includes a chromatographic column, a carrier gas, means for establishing a flow of carrier gas through the column, means for introducing a sample of the mixture to be analyzed into the carrier gas prior to its entry into the column, and a detecting device which is capable of indicating the presence of the various components of the sample both qualitatively and quantitatively as they emerge from the column. All of this is described in greater detail in "Gas Chromatography," by Keulemans, Reinhold, New York (1959), the contents of which are incorporated by reference.

Liquid chromatography is based on separation of the components of a mixture in solution by selective adsorption, and, in some aspects, is similar to gas chromatography except that in liquid chromatography a solvent medium is used instead of the carrier gas utilized in gas chromatography. A typical liquid chromatograph includes a moving solvent, a means for producing solvent motion (i.e., a pump), means for introducing a sample into the solvent prior to its entry into the column, a chromatographic column and a detector. All of this is described in greater detail in "Modern Liquid Chromatography" by Snyder and Kirkland, Wiley Interscience (1974), the contents of which are incorporated by reference.

Both liquid and gas chromatography are widely used for analytical determinations. For example, in many industrial processes, chromatography can be used to detect the presence of impurities in the products obtained at one or more stages of manufacture. Also, boiling range analysis of many products may be obtained quickly and simply by chromatograph. In addition, component-by-component analysis of many materials may be effected by chromatography.

In many of the analysis discussed above, the separation of the components of the sample mixture is enhanced by the application of heat to the chromatographic column. In some analysis, such as boiling point analysis, the rapid and precise application of heat is critical to the accuracy of the analysis.

Prior to the present invention, chromatographic columns were heated via electric resistance elements or ovens. For example, U.S. Pat. No. 3,527,567 of Philyaw describes a gas chromatograph apparatus in which the chromatographic column is heated by placing it in an electric oven.

This method of applying heat to the chromatographic column, however, suffers from serious disadvantages. For example, precise temperatures control over the entire length of the column is different to obtain. In addition, the time it takes to heat the column to the desired temperature may be extremely long, thus limiting the number of analysis that can be conducted on a given piece of equipment during a given time. Finally, in situations where the temperature of the columns are raised throughout the analysis, i.e., the columns are "temperature programmed", the time it takes to cool the oven and columns back to the initial temperature so that another run can be started may be substantial.

In order to alleviate the difficulties outlined above and to provide rapid and substantially uniform heating and cooling of the chromatographic columns, Burow et al., in U.S. Pat. No. 3,232,093, placed the chromatographic column adjacent to a second column which could be cooled by means of a heat exchange fluid. Heat was supplied by wrapping both columns with electrical resistance wire. In U.S. Pat. No. 3,169,389, Green et al. provide a system for the heating of the columns of a gas chromatograph in which the column itself acts as an electrical resistance heating element. Neither of these patents disclose the microwave means for heating chromatograph columns of the present invention.

SUMMARY OF THE INVENTION

It is an object of the present invention to provide a chromatographic apparatus in which heat can be applied to the columns quickly and efficiently, and in which cool-down time is minimized.

The improved chromatograph apparatus of the present invention comprises a column of material which does not reflect microwave radiation, microwave means for heating said column, a carrier fluid, means for establishing a flow of said carrier fluid—which may be either a liquid or a gas—through said column, means for introducing a sample of a material to be analyzed into the column and means for detecting the presence of the separated components of the sample as they are eluted from the column.

With the improved chromatographic apparatus of the present invention which utilizes microwaves rather than the prior art electric resistance devices to apply heat to the chromatographic column, heat can be applied more rapidly than by prior art devices and cool-down time of the equipment is minimized.

One important aspect of the present invention is that the chromatographic columns be made of a material which does not reflect microwaves. Glass and plastics, for example, are materials from which the column can be made since microwaves pass through such materials. In addition, columns can be of ceramic materials which adsorb microwaves. Metals, on the other hand, reflect microwaves and hence cannot be used for the columns of the present invention. Thus, the present invention provide a chromatographic apparatus which is substantially different from prior art apparatus in which the columns are usually made from a metal tube.

BRIEF DESCRIPTION OF THE DRAWING

The drawing is a diagrammatic representation of a specific embodiment of the present invention with various components shown in block form.

For the gas chromatograph embodiment of the present invention, the column generally comprises a tube which contains either a coating of a non-volatile liquid on the inside surface, a bed of solid material or a solid support which is coated with a non-volatile liquid. Columns in which only a liquid phase is utilized are known to the art as capillary columns. Columns which contain solid beds are known as packed columns. In many instances the column comprises a tube having an inside diameter of 4 to 8 mm and a length of from 6 inches to 60 feet or more. Materials which are used for the liquid phase should be stable over the range of temperatures employed in the operation of the column and should not vaporize at the highest column temperature. Examples include silicone rubber gum or silicone oil, polyethylene, squalene and paraffin wax. Materials which are used as the solid support in packed columns are generally crushed to 20 to 200 mesh. Examples include crushed fire brick and diatomaceous earth. Typical column packings include: dimethyl sulfane on fire brick, tricresyl phosphate on fire brick, squalene (2, 6, 10, 15, 19, 23-hexamethyl tetracasane) on fire brick, palladium black on asbestos, activated charcoal, silica gel and molecular sieves.

Columns for liquid chromatograph apparatus also include tubular packed columns. Typical packing materials include silica gel, alumina, glass beads, polystryene gel, and ion exchange resins.

Heat is supplied to the columns of the chromatograph apparatus of the present invention by microwave means which include a magnetron for generating microwaves of a predetermined frequency and a wave guide for transmitting the microwave energy from the output of the magnetron to the column. The column is normally located in an oven defined by side walls, a top wall, a bottom and a door which includes a conventional microwave energy seal to prevent the escape of microwave energy. The walls of the oven are made of materials which reflect microwaves (such as metals) so that when microwaves are introduced into the oven, they are reflected from the walls until they strike and are absorbed by the column or its contents. Thus, very little energy goes to wasteheating the oven itself, as it would in a conventional electric resistance type oven. As previously mentioned, this minimizes cool down times between runs.

The oven further includes temperature setting controls in order that isothermal temperatures may be maintained or temperature programming may be carried out.

As utilized herein, the term carrier fluid refers to carrier gas in the case of gas chromatograph apparatus and to solvent in the case of liquid chromatograph apparatus. Any carrier fluid can be employed in the apparatus of the present invention. Typical examples of carrier gases include helium, hydrogen, nitrogen, argon, carbon dioxide. Typical solvents for liquid chromatography include isooctane, methyl ethyl ketone, acetane/chloroform, tetrahydrofuran, hexane and toluene.

A flow of the carrier fluid is established through the chromatographic column. As is known to the art, for a gas chromatograph, a source of carrier gas is provided along with a regulator in order to establish an even flow of gas. For many applications the flow rate can be as little as ½ ml per minute and as great as 100 ml per minute, depending upon the type of column and column packing material. For the liquid chromatograph, a pump is generally used to establish a flow of the solvent through the column.

In the present apparatus, the sample to be analyzed is introduced to the flow of carrier fluid before it enters the chromatograph column. Any conventional chromatographic method for introducing the sample, such as syringe injection into a septum, a sample charging valve or the like may be used.

Any suitable detecting device that is capable of utilizing some property of the detected component to create an electrical current proportional to its concentration can be used in connection with the chromatograph of the present invention. Commonly employed are differential type detectors which compare a physical property of the carrier fluid with that of the carrier fluid which contains the transported component. Of this type, thermal conductivity detecting cells, density difference detectors, ionization detectors and flame temperature detectors can be used. In liquid chromatography common detecting devices are those that measure UV or refractive index of the fluids. The signal produced by the detector may be amplified and fed to a recorder which produces a graphic representation or profile of the component distribution of the sample.

I claim:

1. A chromatograph apparatus which comprises a column of a material selected from the group consisting of glass, plastic and ceramic which material does not reflect microwave radiation, said column being located within an area defined by side walls, a top wall, a bottom and a door, all of which are made of materials which reflect microwaves, microwave means for heating said column, a carrier fluid, means for establishing a flow of said carrier fluid through said column, means for introducing a sample of a material to be analyzed into said flow of carrier fluid prior to the entry of the fluid into said column and means for detecting the presence of separated components of the sample material as they are eluted from the column.

2. The chromatograph of claim 1 werein said microwave means comprises a magnetron and a wave guide for transmitting the microwave energy from the output of the magnetron to the column.

3. The chromatograph of claim 1 wherein said carrier fluid is a carrier gas.

4. The chromatograph of claim 1 wherein said carrier fluid is a solvent.

5. The chromatograph of claim 1 wherein said column is a capillary column.

6. The chromatograph of claim 1 wherein said column is a packed column.

* * * * *